(12) United States Patent
Scholz et al.

(10) Patent No.: US 7,244,819 B2
(45) Date of Patent: Jul. 17, 2007

(54) FUSION POLYPEPTIDES, VACCINES AND COMPOSITIONS OF FKBP CHAPERONES AND TARGET POLYPEPTIDES

(75) Inventors: Christian Scholz, Penzberg (DE); Herbert Andres, Penzberg (DE); Elke Faatz, Huglfing (DE); Alfred Engel, Tutzing (DE); Urban Schmitt, Oberhausen (DE); Ariuna Bazarsuren, Penzberg (DE); Peter Schaarschmidt, Eberfing (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 72 days.

(21) Appl. No.: 10/179,038

(22) Filed: Jun. 24, 2002

(65) Prior Publication Data

US 2003/0096352 A1 May 22, 2003

(30) Foreign Application Priority Data

Jun. 22, 2001 (EP) ................................. 01115225
Aug. 31, 2001 (EP) ................................. 01120939

(51) Int. Cl.
*C01K 1/00* (2006.01)
(52) U.S. Cl. ..................................................... 530/350
(58) Field of Classification Search ............. 424/192.1, 424/193.1, 194.1, 197.11, 196.11, 195.11, 424/94.1, 94.5; 530/350; 435/183, 233; 536/23.4
See application file for complete search history.

(56) References Cited

U.S. PATENT DOCUMENTS

| | | | | |
|---|---|---|---|---|
| 5,908,626 A | * | 6/1999 | Chang et al. ............. | 424/134.1 |
| 6,153,377 A | * | 11/2000 | Devare et al. ................. | 435/5 |
| 6,207,420 B1 | | 3/2001 | Harrison et al. | |
| 6,248,329 B1 | * | 6/2001 | Chandrashekar et al. | 424/191.1 |

FOREIGN PATENT DOCUMENTS

| | | |
|---|---|---|
| EP | 0 293 249 B1 | 8/1992 |
| WO | WO 93/25533 | 12/1993 |
| WO | WO 98/01349 | 1/1998 |
| WO | WO 98/13496 | 1/1998 |
| WO | WO 00 20606 A | 4/2000 |
| WO | WO 00/28011 | 5/2000 |

OTHER PUBLICATIONS (The Dictionary of Immunology, Herbert et al eds, Academic Press, 1995).*
Feng et al (Infection and Immunity, 64(1):363-365, 1996).*
Ellis, R.W. (Chapter 29 of "VACCINES" Plotkin, S.A. et al. (eds) published by W. B. Saunders company (Philadelphia) in 1988, especially p. 571.*
Kohda et al, Biochemical Engineering Journal, 10:39-45, 2002; see abstract and discussion.*
Weir et al Handbook of Experimental Immunology, vol. 1:Immunochemistry, p. 8.14-8.15.*
Riffkin et al., Gene, 167:279-283, 1995.*
Abaza et al. ,J. of Protein Chemistry, 11(5):433-444, 1992.*
Paul, Fundamental Immunology (Philadelphis & New York, Lippincott-Raven Publishers, 1993) pp. 250 and 1311-1312.*
Cruse et al. Illustrated Dictionary of Immunology (Boca Raton, FL, CRC Press, Inc. 1995) p. 309.*
Cohen et al, PNAS 96(1.*
Attwood (Science, 290:471-473, 2000).*
Beaucage., S.L., et al., *Deoxynucleoside Phosphoramidites—A New Class of Key Intermediates for Deoxypolynucleotide Synthesis*, Department of Chemistry, University of Colorado, pp. 1859-1862.
Fischer, G., *Cyclophilin and Peptidyl-Prolyl Cis-Trans Isomerase are Probably Identical Proteins*, NATURE, vol. 337 Feb. 2, 1989.
Hottenrott, S., et al., *The Escherichia coli SlyD is a Metal Ion-Regulated Peptidyl-Prolyl Cis/Trans-Isomerase*, The Journal of Biological Chemistry, vol. 272, No. 25, Issue of Jun. 20, pp. 15697-15701, 1997.
Kapust, R.B., et al., *Escherichia coli Maltose-Binding Protein is Uncommonly Effective at Promoting the Solubility of Polypeptides to Which it is Fused*, Protein Science (1999), pp. 1668-1674.
Kay, J.E., *Structure-Function Relationships in the FK506-Binding Proteing (FKBP) Family of Peptidylprolyl Cis-Trans Isomerases*, BIOCHEM. J., (1996), 314, 361-385.
Lane, W.S., *Complete Amino Acid Sequence of the FK506 and Rapamycin Binding Protein, FKBP, Isolated from Calf Thymus*, Journal of Protein Chemistry, pp. 151-160, vol. 10, No. 2, 1991.
Maniatis, T., et al., *Molecular Cloning, A Laboratory Manual*, Cold Spring Harbor Laboratory, 1982, Table of Contents, Seven Pages, only table of contents.
Matteucci, M.D., et al., *Synthesis of Deoxyoligonucleotides on a Polymer Support*, Journal of The American Chemical Society, vol. 103, No. 11, 1981.
Metzger D., et al., *The Human Oestrogen Receptor Functions in Yeast*, NATURE, pp. 31-316, vol. 334, Jul. 7, 1988.
Rahfeld, J., et al., *Confirmation of the Existence of a Third Family Among Peptidyl-Prolyl Cisltrans Isomerases Amino Acid Sequence and Recombinant Production of Parvulin*, FEBS Letters, 352 (1994) pp. 180-184.
Ramm, K., et al., *The Periplasmic Escherichia coli Peptidylprolyl Cis, Trans-Isomerase FkpA*, The Journal of Biological Chemistry, vol. 275, No. 22, Issue of Jun. 2, pp. 17106-17113, 2000.

(Continued)

Primary Examiner—Patricia A. Duffy
(74) Attorney, Agent, or Firm—Brinks Hofer Gilson & Lione (57) ABSTRACT

The present invention relates to the cloning and expression of foreign protein or polypeptides in bacteria, such as *Escherichia coli*. In particular, this invention relates to expression tools comprising a FKBP-type peptidyl prolyl isomerase selected from the group consisting of FkpA, SlyD, and trigger factor; methods of recombinant protein expression, the recombinant polypeptides thus obtained, as well as to the use of such polypeptides.

20 Claims, 3 Drawing Sheets

OTHER PUBLICATIONS

Scholz, C., et al., *Cooperation of Enzymatic and Chaperon Functions of Trigger Factor in the Catalysis of Protein Folding*, The EMBO Journal, vol. 16, No. 1, pp. 54-58, 1997.

Spreng S. and Gentschev I., "Construction of Chromosomally Encoded Secreted Hemolysin Fusion Proteins By Use of Mini-TnhlyA$_s$ Transposon," *FEMS Microbiology Letters* (1998) 165:187-192.

Schein C., "Production of Soluble Recombinant Proteins in Bacteria," *Biotechnology Nature* (Nov. 1989) 7(11): 1141-1149.

Nishihara K. et al., "Overexpression of Trigger Factor Prevents Aggregation of Recombinant Proteins in *Escherichia coli*," Applied and Enviromental Microbiology (Mar. 2000) 66(3):884-889.

Arié, J.P., et al., *Molecular Microbiology*, 39(1):199-210 (2001).

* cited by examiner

SEQUENCE LISTING

```
<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: primer 1

<400> SEQUENCE: 1
gcgggtgttc cgggtatccc accgaattc                              29

<210> SEQ ID NO 2
<211> LENGTH: 29
<212> TYPE: DNA
<213> ORGANISM: Artificial Sequence
<220> FEATURE:
<223> OTHER INFORMATION: primer 2

<400> SEQUENCE: 2
gaattcggtg ggatacccgg aacacccgc                              29

<210> SEQ ID NO 3
<211> LENGTH: 61
<212> TYPE: DNA
<213> ORGANISM: Artificial Sequence
<220> FEATURE:
<223> OTHER INFORMATION: primer 2

<400> SEQUENCE: 3
cgggatccgg tggcggttca ggcggtggct ctggtggcgg tacgctgacg gtacaggcca    60
g                                                                    61

<210> SEQ ID NO 4
<211> LENGTH: 30
<212> TYPE: DNA
<213> ORGANISM: Artificial Sequence
<220> FEATURE:
<223> OTHER INFORMATION: primer 4

<400> SEQUENCE: 4
ccgctcgagg taccacagcc aatttgttat                              30

<210> SEQ ID NO 5
<211> LENGTH: 1269
<212> TYPE: DNA
<213> ORGANISM: Artificial Sequence
<220> FEATURE:
<223> OTHER INFORMATION: coding for a FkpA-gp41 fusion protein

<400> SEQUENCE: 5
atggctgaag ctgcaaaacc tgctacaact gctgacagca agcagcgtt caaaaatgac     60 gatcagaaat cagcttatgc actgggtgct tcgctgggtc gttacatgga aaactctctt    120
aaagaacaag aaaaactggg catcaaactg gataagatc agctgatcgc tggtgttcag    180
```

```
gatgcatttg ctgataagag caaactctcc gaccaagaga tcgaacagac tctgcaagca      240
ttcgaagctc gcgtgaagtc ttctgctcag gcgaagatgg aaaagacgc  ggctgataac      300 gaagcaaaag gtaaagagta ccgcgagaaa tttgccaaag agaaggtgt  gaaaccctct      360 tcaactggtc tggtttatca ggtagtagaa gccggtaaag gcgaagcacc gaaagacagc      420
gatactgttg tagtgaacta caaggtacgc tgatcgacg  gtaaagagtt cgacaactct      480
tacacccgtg gtgaaccgct ctctttccgt ctggacggtg ttatcccggg ttggacagaa      540
ggtctgaaga acatcaagaa aggcggtaag atcaaactgg ttattccacc agaactggct      600
tacggcaaag cgggtgttcc gggtatccca ccgaattcta ccctggtgtt tgacgtagag      660
ctgctggatg tgaaaccagc gccgaaggct gatgcaaagc cggaagctga tgcgaaagcc      720
gcagattctg ctaaaaaagg tggcggttcc ggcggtggct ctggtggcgg atccggtggc      780
ggttccggcg gtggctctgg tggcggtacg ctgacggtac aggccagaca attattgtct      840
ggtatagtgc agcagcagaa caatgagctg agggctattg aggcgcaaca gcatctggag      900
caactcacag tctggggcac caagcagctc caggcaagag aactggctgt ggaaagatac      960
ctaaaggatc aacagctcct ggggatttgg ggttgctctg gaaaactcat tgcaccact     1020 gctgtgcctt ggaatgctag ttggagtaat aaatctctgg aacagatttg gaataacatg     1080
acctggatgg agtgggacag agaaattaac aattacacaa gcttaatca  ttccttaatt     1140 gaagaatcgc aaaaccagca agaaaagaat gaacaagaat tattggaatt agataaatgg     1200
gcaagtttgt ggaattggtt taacataaca aattggctgt ggtacctcga gcaccaccac     1260
caccaccac                                                              1269

<210> SEQ ID NO 6
<211> LENGTH: 1026
<212> TYPE: DNA
<213> ORGANISM: Artificial Sequence
<220> FEATURE:
<223> OTHER INFORMATION: coding for a SlyD-gp41 fusion protein

<400> SEQUENCE: 6
atgaaagtag caaaagacct ggtggtcagc ctggcctatc aggtacgtac agaagacggt       60
gtgttggttg atgagtctcc ggtgagtgcg ccgctggact acctgcatgg tcacggttcc      120
ctgatctctg gcctggaaac ggcgctggaa ggtcatgaag ttggcgacaa atttgatgtc      180
gctgttggcg cgaacgacgc ttacggtcag tacgacgaaa acctggtgca acgtgttcct      240
aaagacgtat ttatgggcgt tgatgaactg caggtaggta tgcgtttcct ggctgaaacc      300
gaccagggtc cggtaccggt tgaaatcact gcggttgaag acgatcacgt cgtggttgat      360
ggtaaccaca tgctggccgg tcagaacctg aaattcaacg ttgaagttgt ggcgattcgc      420
gaagcgactg aagaagaact ggctcatggt cacgttcacg gcgcgcacga tcaccaccac      480
gatcacgacc acgacggtgg cggttccggc ggtggctctg gtggcggatc cggtggcggt      540
tccggcggtg gctctggtgg cggtacgctg acggtacagg ccagacaatt attgtctggt      600
atagtgcagc agcagaacaa tgagctgagg gctattgagg cgcaacagca tctggagcaa      660
ctcacagtct ggggcaccaa gcagctccag gcaagagaac tggctgtgga agatacccta      720
aaggatcaac agctcctggg gatttggggt tgctctggaa aactcatttg caccactgct      780
gtgccttgga atgctagttg gagtaataaa tctctggaac agatttggaa taacatgacc      840
tggatggagt gggacagaga aattaacaat tacacaagct taatcattc  cttaattgaa      900 gaatcgcaaa accagcaaga aaagaatgaa caagaattat tggaattaga taaatgggca      960
```
agtttgtgga attggtttaa cataacaaat tggctgtggt acctcgagca ccaccaccac 1020
caccac 1026

<210> SEQ ID NO 7
<211> LENGTH: 367
<212> TYPE: PRT
<213> ORGANISM: Artificial Sequence
<220> FEATURE:
<223> OTHER INFORMATION: single-chain SlyD

<400> SEQUENCE: 7

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp His Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp

```
                    340              345              350
Gly Gly Gly Ser Gly Gly Gly Leu Glu His His His His His
            355              360              365

<210> SEQ ID NO 8
<211> LENGTH: 537
<212> TYPE: PRT
<213> ORGANISM: Artificial Sequence
<220> FEATURE:
<223> OTHER INFORMATION: single-chain FkpA

<400> SEQUENCE: 8

Met Ala Glu Ala Ala Lys Pro Ala Thr Thr Ala Asp Ser Lys Ala Ala
1               5                   10                  15

Phe Lys Asn Asp Asp Gln Lys Ser Ala Tyr Ala Leu Gly Ala Ser Leu
            20                  25                  30

Gly Arg Tyr Met Glu Asn Ser Leu Lys Glu Gln Glu Lys Leu Gly Ile
        35                  40                  45

Lys Leu Asp Lys Asp Gln Leu Ile Ala Gly Val Gln Asp Ala Phe Ala
    50                  55                  60

Asp Lys Ser Lys Leu Ser Asp Gln Glu Ile Glu Gln Thr Leu Gln Ala
65                  70                  75                  80

Phe Glu Ala Arg Val Lys Ser Ser Ala Gln Ala Lys Met Glu Lys Asp
                85                  90                  95

Ala Ala Asp Asn Glu Ala Lys Gly Lys Glu Tyr Arg Glu Lys Phe Ala
            100                 105                 110

Lys Glu Lys Gly Val Lys Thr Ser Ser Thr Gly Leu Val Tyr Gln Val
        115                 120                 125

Val Glu Ala Gly Lys Gly Glu Ala Pro Lys Asp Ser Asp Thr Val Val
    130                 135                 140

Val Asn Tyr Lys Gly Thr Leu Ile Asp Gly Lys Glu Phe Asp Asn Ser
145                 150                 155                 160

Tyr Thr Arg Gly Glu Pro Leu Ser Phe Arg Leu Asp Gly Val Ile Pro
                165                 170                 175

Gly Trp Thr Glu Gly Leu Lys Asn Ile Lys Lys Gly Gly Lys Ile Lys
            180                 185                 190

Leu Val Ile Pro Pro Glu Leu Ala Tyr Gly Lys Ala Gly Val Pro Gly
        195                 200                 205

Ile Pro Pro Asn Ser Thr Leu Val Phe Asp Val Glu Leu Leu Asp Val
    210                 215                 220

Lys Pro Ala Pro Lys Ala Asp Ala Lys Pro Glu Ala Asp Ala Lys Ala
225                 230                 235                 240

Ala Asp Ser Ala Lys Lys Gly Gly Ser Gly Gly Gly Ser Gly Gly Gly
                245                 250                 255

Gly Ser Gly Gly Gly Ser Gly Gly Ser Gly Gly Gly Ser Gly Gly Gly
            260                 265                 270

Gly Ser Gly Gly Gly Ala Glu Ala Ala Lys Pro Ala Thr Thr Ala Asp
        275                 280                 285

Ser Lys Ala Ala Phe Lys Asn Asp Asp Gln Lys Ser Ala Tyr Ala Leu
    290                 295                 300

Gly Ala Ser Leu Gly Arg Tyr Met Glu Asn Ser Leu Lys Glu Gln Glu
305                 310                 315                 320

Lys Leu Gly Ile Lys Leu Asp Lys Asp Gln Leu Ile Ala Gly Val Gln
                325                 330                 335

Asp Ala Phe Ala Asp Lys Ser Lys Leu Ser Asp Gln Glu Ile Glu Gln
```

```
                        340                 345                 350
Thr Leu Gln Ala Phe Glu Ala Arg Val Lys Ser Ser Ala Gln Ala Lys
            355                 360                 365

Met Glu Lys Asp Ala Ala Asp Asn Glu Ala Lys Gly Lys Glu Tyr Arg
    370                 375                 380

Glu Lys Phe Ala Lys Glu Lys Gly Val Lys Thr Ser Ser Thr Gly Leu
385                 390                 395                 400

Val Tyr Gln Val Val Glu Ala Gly Lys Gly Glu Ala Pro Lys Asp Ser
                405                 410                 415

Asp Thr Val Val Val Asn Tyr Lys Gly Thr Leu Ile Asp Gly Lys Glu
                420                 425                 430

Phe Asp Asn Ser Tyr Thr Arg Gly Glu Pro Leu Ser Phe Arg Leu Asp
            435                 440                 445

Gly Val Ile Pro Gly Trp Thr Glu Gly Leu Lys Asn Ile Lys Lys Gly
        450                 455                 460

Gly Lys Ile Lys Leu Val Ile Pro Pro Glu Leu Ala Tyr Gly Lys Ala
465                 470                 475                 480

Gly Val Pro Gly Ile Pro Pro Asn Ser Thr Leu Val Phe Asp Val Glu
                485                 490                 495

Leu Leu Asp Val Lys Pro Ala Pro Lys Ala Asp Ala Lys Pro Glu Ala
                500                 505                 510

Asp Ala Lys Ala Ala Asp Ser Ala Lys Lys Gly Gly Gly Ser Gly Gly
            515                 520                 525

Gly Leu Glu His His His His His His
    530                 535

<210> SEQ ID NO 9
<211> LENGTH: 4
<212> TYPE: PRT
<213> ORGANISM: Artificial Sequence
<220> FEATURE:
<223> OTHER INFORMATION: coagulation factor Xa cleavage site

<400> SEQUENCE: 9

Ile Glu Gly Arg
1

<210> SEQ ID NO 10
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 10

Gly Leu Pro Arg Gly Ser
1               5
```

FUSION POLYPEPTIDES, VACCINES AND COMPOSITIONS OF FKBP CHAPERONES AND TARGET POLYPEPTIDES

RELATED APPLICATIONS

This application claims priority to EP Application No. 01115225.3 filed on Jun. 22, 2001; and EP Application No. 01120939.2 filed on Aug. 31, 2001, both in the European Patent Office, which are incorporated herein by reference in their entirety.

FIELD OF THE INVENTION

The present invention relates to the cloning and expression of a heterologous protein or polypeptide in bacteria such as *Escherichia coli*. In particular, this invention relates to expression tools comprising a FKBP-type peptidyl prolyl isomerase selected from the group consisting of FkpA, SlyD, and trigger factor, methods of recombinant protein expression, the recombinant polypeptides thus obtained, as well as to the use of such polypeptides.

BACKGROUND

A large variety of expression systems has been described in the patent as well as in the scientific literature. However, despite the fact that fusion proteins have become a cornerstone of modern biology, obtaining the target protein in a soluble, biologically active form, as well as in high yield, continues to be a major challenge (Kapust, R. B. and Waugh, D. S., Protein Sci 8 (1999) 1668-74).

Examples of fusion partners that have been touted as solubilizing agents include thioredoxin (TRX), glutathione S-transferase (GST), maltose-binding protein (MBP), Protein A, ubiquitin, and DsbA. Although widely recognized and potentially of great importance, this solubilizing effect remains poorly understood. It is not clear, for example, what characteristics besides intrinsically high solubility epitomize an effective solubilizing agent. Are all soluble fusion partners equally proficient at this task, or are some consistently more effective than others? Similarly, it is not known whether the solubility of many different polypeptides can be improved by fusing them to a highly soluble partner, or whether this approach is only effective in a small fraction of cases.

The state of the art relating to the most potent expression systems has recently been summarized by Kapust et al., supra. In their attempt to produce soluble fusion proteins comprising various target proteins they assessed three different and prominent candidate fusion partners. Maltose-binding protein (MBP), glutathione S-transferase (GST), and thioredoxin (TRX) were tested for their ability to inhibit the aggregation of six diverse proteins that normally accumulate in an insoluble form. All these candidate expression systems are known to the skilled artisan and described in detail elsewhere (e.g., EP 293 249 describes in detail the use of GST as an expression tool).

Remarkably, Kapust et al., supra, found that MBP is a far more effective solubilizing agent than the other two fusion partners also widely used in the art. Moreover, they demonstrated that only in some cases, fusion to MBP can promote the proper folding of the attached protein into its biologically active conformation.

It is especially critical that many aggregation-prone polypeptides may be rendered soluble by fusing them to an appropriate partner, but that some candidate fusion partners in a more or less unpredictable way are much better solubilizing agents than others.

A great demand therefore exists to provide for alternative, efficient expression tools, which are especially appropriate for the recombinant expression of aggregation prone proteins, e.g. like the rsgps.

There is a wealth of patent literature relating to proteins which bind to the immunosupressant FK-506, the so-called FK-506 binding proteins or FKBPs.

These proteins have been extensively studied and commercial applications have been designed centering around the FK-506 binding activity of these proteins. For example, WO 93/25533 makes use of CTP:CMP-3-deoxy-D-manno-octulosonate cytidyl transferase (=CKS) as expression tool. A FKBP is inserted into a CKS-based expression vector down-stream of the CKS gene. The fusion protein obtained is used to improve measurements of FK-506 and other immunosuppressants.

WO 00/28011 discloses materials and methods for regulation of biological events such as target gene transcription and growth, proliferation and differentiation of engineered cells.

WO 97/10253 relates to a high throughput assay for screening of compounds capable of binding to a fusion protein which consists of a target protein and an FK-506-binding protein. Disclosed is the use of an FKBP12-Src homology (SH2) fusion protein in an high throughput screening assay. The fusion protein is produced in soluble form in the bacterial periplasm and released by standard freeze-thaw treatment.

SUMMARY OF THE INVENTION

The present invention in a first embodiment relates to a recombinant DNA molecule, encoding a fusion protein, comprising at least one nucleotide sequence coding for a target polypeptide and upstream thereto at least one nucleotide sequence coding for a FKBP chaperone, characterized in that the FKBP chaperone is selected from the group consisting of FkpA, SlyD and trigger factor.

Preferred ways of designing such recombinant DNA molecules as well as their use as part of an expression vector, a host cell comprising such expression vector, and in the production of fusion polypeptide are also disclosed.

It has in addition been found that the recombinant fusion polypeptides themselves exhibit surprising and advantageous properties, e.g., with regard to solubilization, purification and handling. In a further embodiment the present invention relates to a recombinantly produced fusion protein comprising at least one polypeptide sequence corresponding to a FKBP chaperone selected from the group consisting of FkpA, SlyD and trigger factor and at least one polypeptide sequence corresponding to a target peptide.

A further embodiment relates to a recombinantly produced fusion protein comprising at least one polypeptide sequence corresponding to a FKBP chaperone selected from the group consisting of FkpA, SlyD and trigger factor, at least one polypeptide sequence corresponding to a target polypeptide, and at least one peptidic linker sequence of 10-100 amino acids.

Preferred recombinant fusion polypeptides are also disclosed as well as the use of such fusion polypeptides in various applications.

BRIEF DESCRIPTION OF THE DRAWINGS

UV-spectrum of the fusion polypeptide FkpA-gp41 after dialysis against 50 mM sodium phosphate, pH 2.5; 50 mM NaCl. Surprisingly, the two-domain construct remains completely soluble after removal of the solubilizing chaotropic agent GuHCl. There is no evidence for the existence of light-straying aggregates that would be expected to cause a baseline drift and significant apparent absorption at wavelengths beyond 300 nm.

The spectrum was recorded on a Jasco 720 spectropolarimeter in 20 mM sodium phosphate, pH 2.5; 50 mM NaCl at 20° C. and was accumulated nine times to lower the noise. Protein concentration was 22.5 µM at a path length of 0.5 cm. The aromatic ellipticity shows the typical signature of gp41. At pH 2.5, FkpA is largely unstructured and does not contribute to the signal in the Near-UV-CD at all.

The spectrum was recorded on a Jasco 720 spectropolarimeter in 20 mM sodium phosphate pH 2.5; 50 mM NaCl at 20° C. and was accumulated nine times to improve the signal-to-noise ratio. Protein concentration was 2.25 µM at a path-length of 0.2 cm. The minima at 220 and 208 nm point to a largely helical structure of gp41 in the context of the fusion protein. The spectral noise below 197 nm is due to the high amide absorption and does not report on any structural features of the fusion protein. Nevertheless, the typical helix-maximum at 193 nm can be guessed.

The spectrum was recorded on a Jasco 720 spectropolarimeter in 20 mM sodium phosphate, pH 7.4; 50 mM NaCl at 20° C. and was accumulated nine times to lower the noise. Protein concentration was 15.5 µM at a path-length of 0.5 cm. Strikingly, the aromatic ellipticity of the covalently linked protein domains of g41 and FkpA (continuous line) is made up additively from the contributions of native-like all-helical gp41 at pH 3.0 (lower dashed line) and the contributions of FkpA at pH 7.4 (upper dashed line). This indicates that the carrier FkpA and the target gp41 (i.e. two distinct functional folding units) refold reversibly and quasi-independently when linked in a polypeptide fusion protein.

The spectrum was recorded on a Jasco 720 spectropolarimeter in 20 mm Sodium phosphate, pH 7.4; 50 mM NaCl at 20° C. and accumulated nine times to improve the signal-to-noise ratio. Protein concentration was 1.55 µM at a path-length of 0.2 cm. The strong signals at 222 nm and 208 nm, respectively, point to a largely helical structure of gp41 in the context of the fusion construct. The noise below 198 nm is due to the high protein absorption and does not reflect any secondary structural properties of FkpA-gp41.

CD spectra were recorded on a Jasco-720 spectropolarimeter in 0.5 cm-cuvettes and averaged to improve the signal-to-noise-ratio. Buffer conditions were 50 mM sodium phosphate pH 7.8, 100 mM sodium chloride at 20° C. Protein concentration was 45 µM for both scFkpA (top line at 280 nm) and scSlyD (lower line at 280 nm), respectively. The structural similarity of both proteins is evidenced by the similar signature in the "fingerprint region."

DETAILED DESCRIPTION

The present invention describes novel polypeptide expression systems. In a preferred embodiment it relates to a recombinant DNA molecule, encoding a fusion protein, comprising at least one nucleotide sequence coding for a target polypeptide and upstream thereto at least one nucleotide sequence coding for a FKBP chaperone, characterized in that the FKBP chaperone is selected from the group consisting of FkpA, SlyD and trigger factor.

It was the task of the present invention to investigate whether it is possible to develop and provide efficient alternative expression systems which can be used for improved expression of a recombinant protein comprising a rsgp as a target protein and which at the same time are also appropriate for less critical target proteins.

To our surprise we have been able to identify certain modular members of the FKBP-type family of the peptidyl prolyl isomerase (PPI or PPIase) chaperones as very promising cloning tools. We found that an expression system based on a FKBP-type family of the chaperone selected from the group consisting of SlyD, FkpA, and trigger factor is ideal to express critical proteins like an rsgp and at the same time we could also demonstrate that these chaperones as well represent extremely promising cloning tools for less critical target proteins.

As the skilled artisan will appreciate the term "at least one" is used to indicate that one or more nucleotide sequences coding for a target polypeptide, or for a FKBP chaperone, respectively, may be used in construction of a recombinant DNA molecule without departing from the scope of the present invention. Preferably, the DNA construct will comprise one or two sequences coding for a target polypeptide, one being most preferred, and at the same time, will contain at least one and at most four sequences, coding for a chaperone, one or two being most preferred.

The term "recombinant DNA molecule" refers to a DNA molecule which is made by the combination of two otherwise separated segments of sequence accomplished by the artificial manipulation of isolated segments of polynucleotides by genetic engineering techniques or by chemical synthesis. In so doing, one may join together polynucleotide segments of desired functions to generate a desired combination of functions.

Large amounts of the polynucleotides may be produced by replication in a suitable host cell. Natural or synthetic DNA fragments coding for proteins or fragments thereof will be incorporated into recombinant polynucleotide constructs, typically DNA constructs, capable of introduction into and replication in a prokaryotic or eukaryotic cell.

The polynucleotides may also be produced by chemical synthesis, including, but not limited to, the phosphoramidite method described by Beaucage, S. L. and Caruthers, M. H., Tetrahedron Letters 22 (1981) 1859-1862 and the triester method according to Matteucci, M. D. and Caruthers, M. H., J. Am. Chem. Soc. 103 (1981) 3185-3191. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

A polynucleotide is said to "encode" a polypeptide if, in its native state or when manipulated by methods known in the art, the polynucleotide can be transcribed and/or translated to produce the polypeptide or a fragment thereof.

A target polypeptide according to the present invention may be any polypeptide required in larger amounts and therefore difficult to isolate or purify from other non-recombinant sources. Examples of target proteins preferably produced by the present methods include mammalian gene products, such as enzymes, cytokines, growth factors, hormones, vaccines, antibodies and the like. More particularly, preferred overexpressed gene products of the present invention include gene products such as erythropoietin, insulin, somatotropin, growth hormone releasing factor, platelet derived growth factor, epidermal growth factor, transforming growth factor a, transforming growth factor 13, epidermal growth factor, fibroblast growth factor, nerve growth factor, insulin-like growth factor I, insulin-like growth factor II, clotting Factor VIII, superoxide dismutase, α-interferon, y-interferon, interleukin-1, interleukin-2, interleukin-3, interleukin-4, interleukin-5, interleukin-6, granulocyte colony stimulating factor, multi-lineage colony stimulating activity, granulocyte-macrophage stimulating factor, macrophage colony stimulating factor, T cell growth factor, lymphotoxin and the like. Preferred overexpressed gene products are human gene products. Moreover, the present methods can readily be adapted to enhance secretion of any overexpressed gene product which can be used as a vaccine. Overexpressed gene products which can be used as vaccines include any structural, membrane-associated, membrane-bound or secreted gene product of a mammalian pathogen. Mammalian pathogens include viruses, bacteria, single-celled or multi-celled parasites which can infect or attack a mammal. For example, viral vaccines can include vaccines against viruses such as human immunodeficiency virus (HIV), vaccinia, poliovirus, adenovirus, influenza, hepatitis A, hepatitis B, dengue virus, Japanese B encephalitis, *Varicella zoster*, cytomegalovirus, hepatitis A, rotavirus, as well as vaccines against viral diseases like measles, yellow fever, mumps, rabies, herpes, influenza, parainfluenza and the like. Bacterial vaccines can include vaccines against bacteria such as *Vibrio cholerae, Salmonella typhi, Bordetella pertussis, Streptococcus pneumoniae, Hemophilus influenza, Clostridium tetani, Corynebacterium diphtheriae, Mycobacterium leprae, R. rickettsii, Shigella, Neisseria gonorrhoeae, Neisseria meningitidis, Coccidioides immitis, Borellia burgdorferi*, and the like.

Preferably, the target protein is a member of a group consisting of HIV-1 gp41, HIV-2 gp36, HTLV gp21, HIV-1 p17, SlyD, FkpA, and trigger factor.

A target polypeptide according to the present invention may also comprise sequences, e.g., diagnostically relevant epitopes, from several different proteins constructed to be expressed as a single recombinant polypeptide.

The folding helpers termed peptidyl prolyl isomerases (PPIs or PPIases) are subdivided into three families, the parvulines (Schmid, F. X., Molecular chaperones in the life cyle of proteins (1998) 361-389, Eds. A. L. Fink and Y. Goto, Marcel Decker In., New York), Rahfeld, J. U., et al., FEBS Lett 352 (1994) 180-4) the cyclophilines (Fischer, G., et al., Nature 337 (1989) 476-8, and the FKBP family (Lane, W. S., et al., J Protein Chem 10 (1991) 151-60). The FKBP family exhibits an interesting biochemical feature since its members have originally been identified by their ability to bind to macrolides, e.g., FK 506 and rapamycin (Kay, J. E., Biochem J 314 (1996) 361-85).

According to the present invention, the preferred modular PPIases are FkpA (Ramm, K. and Pluckthun, A., J Biol Chem 275 (2000) 17106-13), SlyD (Hottenrott, S., et al., J Biol Chem 272 (1997) 15697-701) and trigger factor (Scholz, C., et al., Embo J 16 (1997) 54-8), all members of the FKBP family. Most preferred are the chaperones FkpA and SlyD.

It is also well known and appreciated that it is not necessary to always use the complete sequence of a molecular chaperone. Functional fragments of chaperones (so-called modules), which still possess the required abilities and functions, may also be used (cf. WO 98/13496).

For instance, FkpA is a periplasmic PPI that is synthesized as an inactive precursor molecule in the bacterial cytosol and translocated across the cytoplasmic membrane. The active form of FkpA (mature FkpA or periplasmic FkpA) lacks the signal sequence (amino acids 1 to 25) and thus comprises amino acids 26 to 270 of the precursor molecule. Relevant sequence information relating to FkpA can easily be obtained from public databases, e.g., from "SWISS-PROT" under accession number P45523. The FkpA used as expression tool according to the present invention lacks the N-terminal signal sequence.

A close relative of FkpA, namely SlyD, consists of a structured N-terminal domain responsible for catalytic and chaperone functions and of a largely unstructured C-terminus that is exceptionally rich in histidine and cysteine residues (Hottenrott, supra). We found that a C-terminally truncated variant of SlyD comprising amino acids 1-165 exerts exceptionally positive effects on the efficient expression of target proteins. Unlike in the wild-type SlyD, the danger of compromising disulfide shuffling is successfully circumvented in the truncated SlyD-variant (1-165) used. A recombinant DNA molecule comprising a truncated SlyD (1-165) represents a preferred embodiment of the present invention.

In a preferred mode of designing a DNA construct according to the present invention, no signal peptides are included. The expression systems according to the present invention have been found most advantageous when working as cytosolic expression system. This cytosolic expression results in the formation of inclusion bodies. Different from the pronounced and well-known problems usually associated with inclusion bodies, we now have found that not only an exceptionally high amount of protein is produced, but that the recombinant proteins according to the present invention are also easy to handle, e.g., easy to solubilize and to refold. In a preferred embodiment the present invention thus relates to a recombinant DNA molecule, encoding a fusion protein, comprising at least one nucleotide sequence coding for a target polypeptide and upstream thereto at least one nucleotide sequence coding for a FKBP chaperone, wherein the FKBP chaperone is selected from the group consisting of FkpA, SlyD and trigger factor further characterized in that the DNA construct lacks a signal peptide.

The term "lacks a signal peptide" must not be understood as an undue limitation. As the skilled artisan will readily appreciate either the construct may in fact lack the signal peptide sequence. As an alternative, however, the sequence may simply be modified to lack signal peptide function.

Variants of the above-discussed chaperones, bearing one or several amino acid substitutions or deletions, may also be used to obtain a recombinant DNA or a fusion polypeptide according to the present invention. The skilled artisan can easily assess whether such variants, e.g., fragments or mutants of chaperones or chaperones from alternative sources, are appropriate for a method of the invention by using the procedures as described in the Examples section.

The term "recombinant" or "fusion polypeptide" as used in the present invention, refers to a polypeptide comprising at least one polypeptide domain corresponding to the FKBP-chaperone used as expression tool and at least one polypeptide domain corresponding to the target protein. Optionally such fusion proteins may additionally comprise a linker polypeptide of 10-100 amino acid residues. As the skilled artisan will appreciate, such a linker polypeptide is designed as most appropriate for the intended application, especially in terms of length, flexibility, charge, and hydrophilicity.

Preferably, the DNA construct of the present invention encodes a fusion protein comprising a polypeptide linker in between the polypeptide sequence corresponding to the FKBP-chaperone and the polypeptide sequence corresponding to the target protein. Such a DNA sequence coding for a linker, in addition to e.g., providing for a proteolytic cleavage site, may also serve as a polylinker, i.e., it may provide multiple DNA restriction sites to facilitate fusion of the DNA fragments coding for a target protein and a chaperone domain.

The present invention makes use of recombinant DNA technology in order to construct appropriate DNA molecules.

In a further preferred embodiment the present invention relates a recombinant DNA molecule, encoding a fusion protein, comprising operably linked at least one nucleotide sequence coding for a target polypeptide and upstream thereto at least one nucleotide sequence coding for a FKBP chaperone, characterized in that the FKBP chaperone is selected from the group consisting of FkpA, SlyD and trigger factor.

Polynucleotide sequences are operably-linked when they are placed into a functional relationship with another polynucleotide sequence. For instance, a promoter is operably-linked to a coding sequence if the promoter affects transcription or expression of the coding sequence. Generally, operably-linked means that the linked sequences are contiguous and, where necessary to join two protein coding regions, both contiguous and in reading frame. However, it is well known that certain genetic elements, such as enhancers, may be operably-linked even at a distance, i.e., even if not contiguous.

As the skilled artisan will appreciate it is often advantageous to design a nucleotide sequence coding for a fusion protein such that one or a few, e.g., up to nine, amino acids are located in between the two polypeptide domains of said fusion protein. Fusion proteins thus constructed, as well as the DNA molecules encoding them, obviously are also within the scope of the present invention.

DNA constructs prepared for introduction into a host typically comprise a replication system recognized by the host, including the intended DNA fragment encoding the desired target fusion peptide, and will preferably also include transcription and translational initiation regulatory sequences operably-linked to the polypeptide encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences.

The appropriate promoter and other necessary vector sequences are selected so as to be functional in the host. Examples of workable combinations of cell lines and expression vectors include but are not limited to those described Sambrook, J., et al., in "Molecular Cloning: A Laboratory Manual" (1989)-, Eds. J. Sambrook, E. F. Fritsch and T. Maniatis, Cold Spring Harbor Laboratory Press, Cold Spring Harbor, or Ausubel, F., et al., in "Current Protocols in Molecular Biology" (1987 and periodic updates), Eds. F. Ausubel, R. Brent and K. R. E., Wiley & Sons Verlag, New York; and Metzger, D., et al., Nature 334 (1988) 31-6. Many useful vectors for expression in bacteria, yeast, mammalian, insect, plant or other cells are known in the art and may be obtained from vendors including, but not limited to, Stratagene, New England Biolabs, Promega Biotech, and others. In addition, the construct may be joined to an amplifiable gene (e.g., DHFE) so that multiple copies of the gene may be obtained.

Expression and cloning vectors will likely contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and/or grow under selective conditions. Typical selection genes include but are not limited to those encoding proteins that (a) confer resistance to antibiotics or other toxic substances, e.g., ampicillin, tetracycline, etc.; (b) complement auxotrophic deficiencies; or (c) supply critical nutrients not available from complex media. The choice of the proper selectable marker will depend on the host cell, and appropriate markers for different hosts are known in the art.

The vectors containing the polynucleotides of interest can be introduced into the host cell by any method known in the art. These methods vary depending upon the type of cellular host, including but not limited to transfection employing calcium chloride, rubidium chloride, calcium phosphate, DEAE-dextran, other substances, and infection by viruses. Large quantities of the polynucleotides and polypeptides of the present invention may be prepared by expressing the polynucleotides of the present invention in vectors or other expression vehicles in compatible host cells. The most commonly used prokaryotic hosts are strains of *Escherichia coli*, although other prokaryotes, such as *Bacillus subtilis* may also be used. Expression in *Escherichia coli* represents a preferred mode of carrying out the present invention.

Construction of a vector according to the present invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

In a preferred embodiment, a recombinant DNA molecule according to the present invention comprises a single nucleotide sequence coding for a FKBP-chaperone selected from the group consisting of FkpA, SlyD, and trigger factor and a single nucleotide sequence coding for a target polypeptide.

A fusion protein comprising two FKBP-chaperone domains and one target protein domain is also very advantageous. In a further preferred embodiment the recombinant DNA molecule according to the present invention comprises two sequences coding for a FKBP-chaperone and one sequence coding for a target polypeptide.

The DNA molecule may be designed to comprise both the DNA sequences coding for the FKBP-chaperone upstream to the target protein. Alternatively the two FKBP-domains may be arranged to sandwich the target protein. The construct comprising both FKBP-domains upstream to the target protein represents a preferred embodiment according to the present invention.

The DNA construct comprising two chaperone domains as well as a target polypeptide domain preferably also contains two linker peptides in between these domains. In order to allow for systematic cloning, the nucleotide sequences coding for these two linker peptide sequences preferably are different. This difference in nucleotide sequence must not necessarily result in a difference in the amino-acid sequence of the linker peptides. In yet a further preferred embodiment the amino acid sequences of the two linker peptides are identical. Such identical linker peptide sequences for example are advantageous if the fusion protein comprising two FKBP-chaperone domains as well as their target protein domain is to be used in an immunoassay.

In cases where it is desired to release one or all of the chaperones out of a fusion protein according to the present invention, the linker peptide is constructed to comprise a proteolytic cleavage site. A recombinant DNA molecule encoding a fusion protein comprising at least one polypeptide sequence coding for a target polypeptide, upstream thereto at least one nucleotide sequence coding for a FKBP-chaperone selected from the group consisting of FkpA, SlyD, and trigger factor, and additionally comprising a nucleic acid sequence coding for a peptidic linker comprising a proteolytic cleavage site, represents a further embodiment of this invention.

An expression vector comprising operably-linked to a recombinant DNA molecule according to the present invention, i.e., a recombinant DNA molecule encoding a fusion protein comprising at least one polynucleotide sequence coding for a target polypeptide and upstream thereto at least one nucleotide sequence coding for a FKBP-chaperone, wherein the FKBP-chaperone is selected from FkpA, SlyD, and trigger factor, has proven to be very advantageous.

The expression vector comprising a recombinant DNA according to the present invention may be used to express the fusion protein in a cell-free translation system or may be used to transform a host cell. In a preferred embodiment, the present invention relates to a host cell transformed with an expression vector according to the present invention.

In a further preferred embodiment, the present invention relates to a method of producing a fusion protein. Said method comprises the steps of culturing a host cell transformed with an expression vector according to the present invention, expression of that fusion protein in the respective host cell and purification of said fusion protein.

As discussed above, the FKBP-chaperone domain of FkpA, SlyD, or trigger factor, respectively, is naturally or artificially constructed to yield a cytosolic fusion polypeptide expression. The fusion protein thus produced is obtained in form of inclusion bodies. Whereas in the art, tremendous efforts are spent to obtain any desired recombinant protein or the fusion protein directly in a soluble form, we have found that the fusion protein according to the present invention is easily obtained in soluble form from inclusion bodies. In a further preferred embodiment the present invention therefore relates to a method of producing a fusion protein according to the steps described above, wherein said fusion protein is purified from inclusion bodies.

The purification of fusion protein from inclusion bodies is easily achieved and performed according to standard procedures known to the skilled artisan, like chaotropic solubilization and various ways of refolding.

Isolation and purification of the fusion protein starts from solubilizing buffer conditions, i.e. from a buffer wherein the inclusion bodies, i.e., the fusion protein, are/is solubilized. An appropriate buffer, which may be termed "non-physiological" or "solubilizing" buffer has to meet the requirement that both the target protein and the FKBP chaperone are not irreversibly denatured. Starting from such buffer conditions, the chaperone is in close proximity to the target protein, and a change of the buffer conditions from non-physiological to physiological conditions is possible without precipitation of the fusion protein.

An appropriate (non-physiological) buffer, i.e., a buffer wherein both the target protein which is essentially insoluble and the PPI-chaperone are soluble either makes use of high or low pH, or of a high chaotropic salt concentration or of a combination thereof. The solubilizing buffer preferably is a buffer with rather a high concentration of a chaotropic salt, e.g., 6.0 M guanidinium chloride at a pH of about 6. Upon renaturation, both the target protein as well as the chaperone assume their native-like structure, and the chaperone exerts its positive solubilizing effect.

In the context of this invention, physiological buffer conditions are defined by a pH value between 5.0 and 8.5, and a total salt concentration below 500 mM, irrespective of other non-salt ingredients that optionally may be present in the buffer (e.g., sugars, alcohols, detergents) as long as such additives do not impair the solubility of the fusion protein comprising the target protein and the chaperone.

A variety of target proteins has been expressed in large amounts.

The expression system, according to the present invention, for example, has been shown to work extremely well with biochemically rather different target proteins, e.g., SlyD, FkpA (proteins which are readily soluble), HIV-1 p17 (a protein which is difficult to express in high amounts using conventional expression systems), HTLV gp21 (a protein which tends to aggregate), and HIV-1 gp41, as well as HIV-2 gp36 (both proteins are extremely prone to aggregation and essentially insoluble under physiological buffer conditions). As can be easily gathered from Example 4 specifically relating to these proteins, the efficient expression systems, according to the present invention, work and result in high levels of fusion protein produced. Similar positive findings have been made with a variety of other target proteins expressed as a fusion protein, according to the present invention.

From the list of positive examples, it becomes readily obvious that the novel expression system as disclosed in the present invention, provide for extremely attractive universal expression systems.

The expression systems, as disclosed herein, also have been compared to standard expression systems making use of carrier proteins as recommended in the art, like MBP. It has been found that the novel systems with the target polypeptides tested are quite advantageous. The relative yield of fusion protein produced according to the present invention was at least as good, and in the majority of cases, even higher as compared to the relative yield using MBP-based expression. Efficacy of expression can be assessed both in terms of yield of fusion protein, e.g., per gram of *E. coli* cell mass or on a molar basis, comparing the concentrations of a target protein comprised in different fusion proteins.

The present invention in a preferred embodiment relates to a recombinantly produced fusion protein comprising at least one polypeptide sequence corresponding to a FKBP chaperone selected from the group consisting of FkpA, SlyD and trigger factor and at least one polypeptide sequence corresponding to a target peptide.

It has been found that the fusion proteins according to the present invention exhibit advantageous properties, thus e.g., facilitating production, handling and use of otherwise critical proteins. This becomes readily obvious from the description of the positive results obtained with a fusion protein comprising HIV-1 gp41. Whereas recombinantly-produced gp41 itself is essentially insoluble, it is readily soluble if present as part of a fusion protein according to the present invention.

In general a protein is considered "essentially insoluble" if in a buffer consisting of 20 mM sodium phosphate pH 7.4, 150 mM NaCl, it is soluble in a concentration of 50 nM or less. A fusion protein according to the present invention comprising a FKBP chaperone and a target protein is considered "soluble" if, under physiological buffer conditions, e.g., in a buffer consisting of 20 mM sodium phosphate pH 7.4, 150 mM NaCl the target protein comprised in the PPI-chaperone complex is soluble in a concentration of 100 nM or more.

We found that the recombinantly-produced fusion protein, according to the present invention, can be readily obtained from inclusion bodies in soluble form, even if the target protein is an aggregation-prone protein, like HIV-1 gp41. A striking feature of gp41 comprised in a recombinantly-produced FkpA-gp41 is its exceptional solubility at physiological buffer conditions as compared to the "unchaperoned" gp41 ectodomain.

Moreover, it has been possible to demonstrate that the target protein comprised in a fusion protein, according to the present invention, readily can be obtained in a native-like structure. Such native-like structure, e.g., for HIV-1 gp41 has been confirmed by Near-UV-CD or by its immunoreactivity. Near-UV-CD analysis has shown the typical "gp41-signature," which is known to the skilled artisan.

The fusion protein according to the present invention also is very easy to handle, e.g., it is quite easy to renature such fusion protein. It is interesting that the "chaotropic material" (i.e. FkpA-gp41 in 6.0-7.0 M GuHCl) can be refolded in different ways, all resulting in a thermodynamically stable and soluble native-like form. Refolding is achieved at high yields, both by dialysis and by rapid dilution, as well as by renaturing size exclusion chromatography or matrix-assisted refolding. These findings suggest that in this covalently linked form, the gp41-FkpA fusion polypeptide is a thermodynamically stable rather than a metastable protein.

Some of the FKBP-chaperones (e.g., FkpA) exert their chaperone function in form of oligomers, i.e., in a complex comprising two or more noncovalently associated FKBP polypeptides. We have surprisingly found that it is possible to design and produce such an active FKBP-dimer as a single fusion protein on one and the same polypeptide. We have termed these constructs single-chain PPIs, or single-chain FKBPs. The single-chain PPI comprising two SlyD domains therefore is termed scSlyD and the single-chain PPI comprising two FkpA domains therefore is termed scFkpA. A single-chain peptidyl-prolyl-isomerase, i.e. a fusion protein comprising two PPI-domains represents a very advantageous and therefore preferred embodiment of the present invention. The sc-PPI according to the present invention may be a parvuline, a cyclophyline or a FKBP. The sc-PPIs selected from the FKBP family of chaperones are preferred. Most preferred are sc SlyD and Sc FkpA, respectively.

A recombinantly produced fusion protein comprising at least one polypeptide sequence corresponding to a FKBP chaperone selected from the group consisting of FkpA, SlyD and trigger factor, at least one polypeptide sequence corresponding to a target polypeptide, and at least one peptidic linker sequence of 10-100 amino acids represents a further preferred embodiment of the present invention.

As the skilled artisan will appreciate, the peptidic linker may be constructed to contain the amino acids which are most appropriate for the required application. E.g., in case of a hydrophobic target protein the linker polypeptide preferably will contain an appropriate number of hydrophilic amino acids. The present invention specifically also relates to fusion proteins which comprise the target polypeptide and one, or two FKBP-chaperones or chaperone domains and an appropriate peptidic linker sequences between domains. For such applications where the target protein is required in free form a linker peptide or linker peptides are used, which contain an appropriate proteolytic cleavage site. Peptide sequences appropriate for proteolytic cleavage are well-known to the skilled artisan and comprise amongst others, e.g., Ile-Glu-Gly-Arg (SEQ ID NO:9), cleaved at the carboxy side of the arginine residue by coagulation factor Xa, or Gly-Leu-Pro-Arg-Gly-Ser, (SEQ ID NO:10), a thrombin cleavage site, etc.

As mentioned above the fusion proteins according to the present invention can easily be obtained from inclusion bodies following a simple refolding scheme. They are readily soluble and target polypeptides comprised in such fusion proteins can easily be obtained in native-like confirmation. This is quite advantageous for polypeptides derived from an infectious organism because such native-like polypeptides are most advantageous in diagnostic as well as in therapeutic applications. In a preferred embodiment, the fusion protein, according to the present invention, is further characterized in that a target protein is a polypeptide of interest as known from an infectious organism. Preferred infectious organisms, according to the present invention, are HIV, HTLV, and HCV.

From the scientific as well as from the patent literature it is well-known which peptide sequences contain diagnostically relevant epitopes. For the skilled artisan it is nowadays no problem to identify such relevant epitopes. In a further preferred embodiment the target protein corresponding to a polypeptide derived from an infectious organism will contain at least one diagnostically relevant epitope.

Due to their advantageous properties the recombinantly-produced fusion proteins according to the present invention in further preferred embodiments are used for the immunization of laboratory animals, in the production of a vaccine or in an immunoassay, respectively.

In case a therapeutic application of the novel fusion proteins is intended, preferably a composition comprising a recombinantly-produced fusion protein according to the present invention and a pharmaceutically acceptable excipient are formulated.

The following examples, references, sequence listing and figures are provided to aid the understanding of the present invention, the true scope of which is set forth in the appended claims. It is understood that modifications can be made in the procedures set forth without departing from the spirit of the invention.

EXAMPLES

Example 1

Recombinant Production of HIV-1 gp41 Using a FkpA-Based Expression System 1.1 Construction of an Expression Plasmid Comprising FkpA and gp41

Wild-type FkpA was cloned, expressed and purified according to Bothmann and Plückthun, *J Biol Chem* 275 (2000) 17106-17113 with some minor modifications. For storage, the protein solution was dialyzed against 20 mM $NaH_2PO_4$/NaOH (pH 6.0), 100 mM NaCl and concentrated to 26 mg/ml (1 mM).

For cytosolic expression, the FkpA-coding sequence of the above expression vector was modified to lack the sequence part coding for the signal peptide and to comprise instead only the coding region of mature FkpA.

In the first step, the restriction site BamHI in the coding region of the mature *E. coli* FkpA was deleted using the QuikChange site-directed mutagenesis kit of Stratagene (La Jolla, Calif.; USA) with the primers:

```
5'-gcgggtgttccgggtatcccaccgaattc-3'  (SEQ ID NO:1)

5'-gaattcggtgggatacccggaacacccgc-3'  (SEQ ID NO:2)
```

The construct was named EcFkpA(Δ BamHI)[GGGS]$_3$.

HIV-1 gp41 (535-681)-His$_6$ was cloned and expressed in a T7 promotor-based expression system. The gene fragment encoding amino acids 535-681 from HIV-1 envelope protein was amplified by PCR from the T7-based expression vector using the primers:

```
                                                    (SEQ ID NO:3)
5'-cgggatccggtggcggttcaggcggtggctctggtggcggtacgctg
acggtacaggccag-3'

(SEQ ID NO:4)
5'-ccgctcgaggtaccacagccaatttgttat-3'
```

The fragment was inserted into EcFkpA(Δ BamHI) [GGGS]$_3$ using BamHI and XhoI restriction sites.

The codons for a glycine-serine-rich linker [GGGS]$_3$ between FkpA and e-gp41 were inserted with reverse primer for cloning of FkpA and with forward primer for cloning of e-gp41.

The resulting construct was sequenced and found to encode the desired protein. Variants of this protein have also been generated by site-directed mutagenesis according to standard procedures. A variant of gp41 comprising four amino acid substitutions as compared to the wild-type sequence is, e.g., encoded by the DNA-constructs of SEQ ID NO:5 and 6, making use of FkpA or SlyD as expression system, respectively.

1.2 Purification of the FkpA-gp41 Fusion Protein from *E. coli* Cells

*E. coli* BL21 cells harboring the expression plasmid were grown to an OD$_{600}$ of 0.7, and cytosolic overexpression was induced by adding 1 mM of IPTG at a growth temperature of 37° C. Four hours after induction, the cells were harvested by centrifugation (20 min at 5000 g). The bacterial pellet was resuspended in 50 mM sodium phosphate pH 7.8, 6.0 M GuHCl (guanidinium chloride), 5 mM imidazole and stirred at room temperature (10 min) for complete lysis. After repeated centrifugation (Sorvall SS34, 20000 rpm, 4° C.), the supernatant was filtered (0.8/0.2 µm) and applied to a Ni-NTA-column (NTA: Nitrilotriacetate; Qiagen; Germantown, Md.), pre-equilibrated in lysis buffer. Unspecifically bound proteins were removed in a washing step by applying 10 column volumes of lysis buffer. Finally, the bound target protein was eluted with 50 mM sodium phosphate, pH 2.5, 6.0 M GuHCl and was collected in 4 ml fractions. The absorbance was recorded at 280 nm.

The resulting acidic and chaotropic solution may be stored at 4° C. for further purification steps or in vitro refolding experiments.

Starting with this unfolded material, different refolding methods, such as dialysis, rapid dilution, renaturing size exclusion chromatography or matrix-assisted refolding can be used and carried out successfully, all of them leading to virtually the same native-like folded and soluble protein.

1.3 Renaturation by Dialysis and Rapid Dilution

Material, solubilized as described above, is transferred into physiological buffer conditions by dialysis. The chosen cut-off value of the dialysis tubing was 4000-6000 Daltons.

Figure 1:
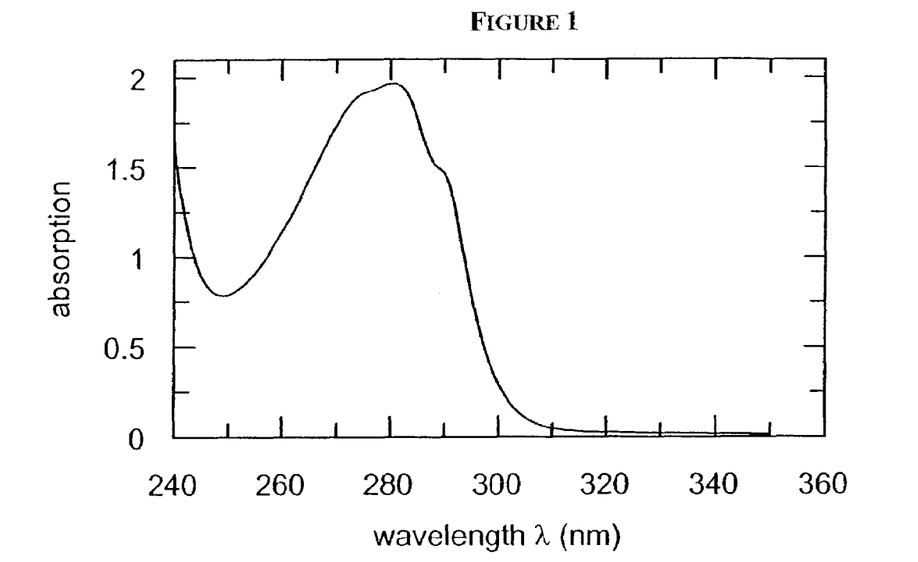
FIG. 1 UV spectrum of FkpA-gp41 at pH 2.5

To induce refolding of the ectodomain (the HIV-1 gp41 part of the fusion protein), GuHCl was removed from the eluted protein by dialysis against 50 mM sodium phosphate, pH 2.5, 50 mM NaCl (sodium chloride). It is well known that the isolated ectodomain is all-helical and forms tertiary contacts at this extreme pH. When analyzing recombinantly-produced FkpA by means of near UV CD, it was found that FkpA is essentially unstructured under the same conditions. It is surprising that refolding of gp41-FkpA by dialysis results in a readily soluble protein complex comprising the covalently linked gp41 and FkpA protein domains. The UV spectrum (FIG. 1) lacks stray light, i.e., apparent absorption beyond 300 nm. Stray light would be indicative of aggregates, thus the spectrum shown in FIG. 1 implies that the re-folded material does not contain significant amounts of aggregates.

Circular dichroism spectroscopy (CD) is the method of choice to assess both secondary and tertiary structure in proteins. Ellipticity in the aromatic region (260-320 nm) reports on tertiary contacts within a protein (i.e., the globular structure of a regularly folded protein), whereas ellipticity in the amide region reflects regular repetitive elements in the protein backbone, i.e., secondary structure.

Figure 2:
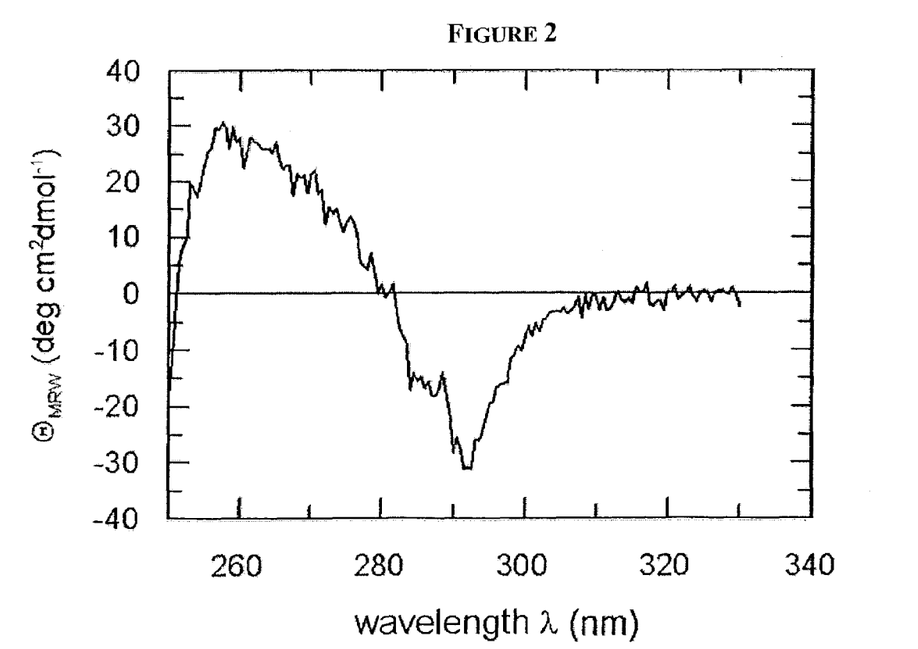
FIG. 2 Near UV CD spectrum of FkpA-gp41 at pH 2.5

The near UV CD spectrum shown in FIG. 2 provides compelling evidence that the ectodomain (in the context of the fusion protein) displays native-like tertiary contacts at pH 2.5. The spectrum of the covalently linked gp41/FkpA protein domains almost coincides with the spectrum of the isolated ectodomain under identical conditions (data not shown). The typical signature of gp41 was found: a maximum of ellipticity at 290 nm, a characteristic shoulder at 285 nm and another maximum at 260 nm reflecting an optically active disulfide bridge. It is important to note that FkpA does not contribute to the near UV signal at all under the respective conditions. In fact, the aromatic ellipticity of FkpA at pH 2.5 virtually equals the baseline (data not shown).

Figure 3:
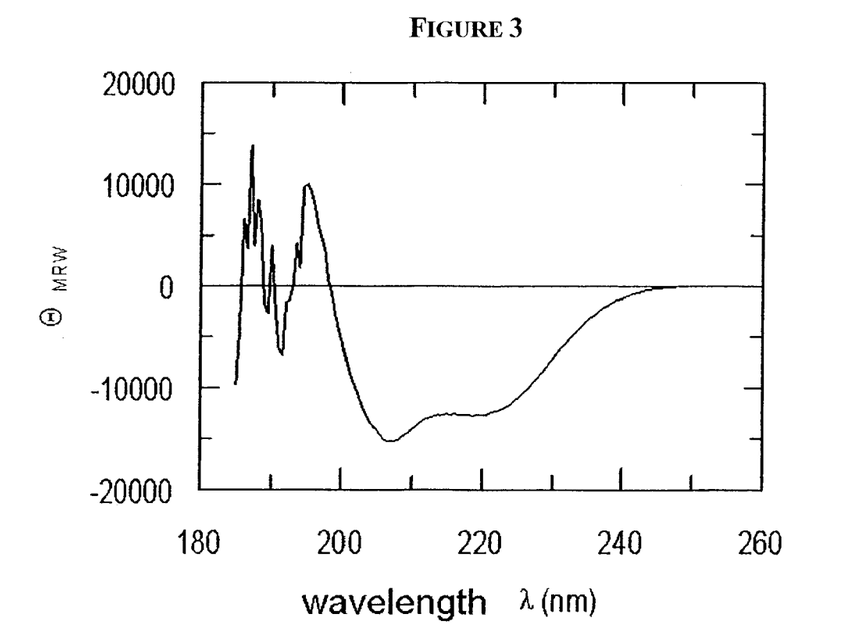
FIG. 3 Far UV CD spectrum of FkpA-gp41 at pH 2.5

In agreement with the results from the near UV region, the far UV CD of the fusion construct at pH 2.5 points to a largely structured gp41 molecule. The two maxima at 220 nm and 208 nm make up, and correspond to, the typical signature of an all-helical ectodomain (FIG. 3). From the conditions indicated (50 mM sodium phosphate, pH 2.5, 50 mM NaCl), the FkpA-gp41 fusion polypeptide can easily be transferred to physiological buffer conditions by rapid dilution. In conclusion, both near and far UV CD underline that native-like structured gp41 is available (in the context of the fusion protein also containing FkpA) in a very convenient fashion.

1.4 Renaturation by Size Exclusion Chromatography (SEC)

Figure 4:
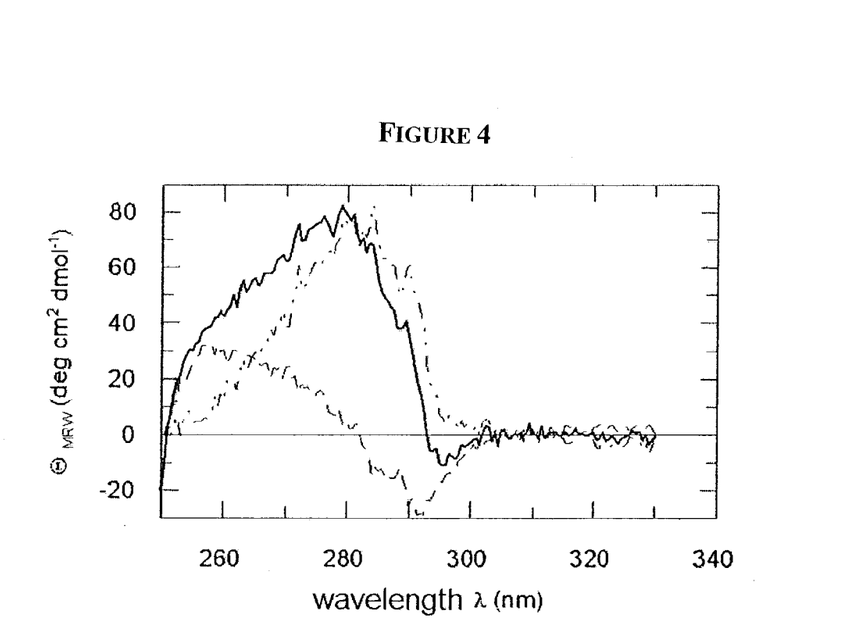
FIG. 4 Near UV CD of FkpA-gp41 under physiological buffer conditions.

Unfolded gp41-FkpA polypeptide (dissolved in 50 mM sodium phosphate, pH 7.8, 7.0 M GuHCl) was applied onto a Superdex 200 gel filtration column equilibrated with 20 mM sodium phosphate, pH 7.4, 50 mM NaCl, 1 mM EDTA. FkpA-gp41 elutes essentially in three main fractions: as a high molecular associate, as an apparent hexamer species and as an apparent trimer species. The apparent trimer fraction was concentrated and assessed for its tertiary structure in a near UV CD measurement (FIG. 4).

The resulting graph is virtually an overlay curve to which both the carrier protein FkpA and the target protein gp41 contribute in a 1:1 ratio. Most fortunately, gp41 displays tertiary structure at neutral pH and is evidently solubilized by the covalently bound chaperone. In other words, the chaperone FkpA seems to accept the native-like structured ectodomain gp41 as a substrate and to solubilize this hard-to-fold protein at a neutral working pH. Thus, a crucial requirement for producing high amounts of soluble gp41 antigen for diagnostic purposes is fulfilled.

Figure 5:
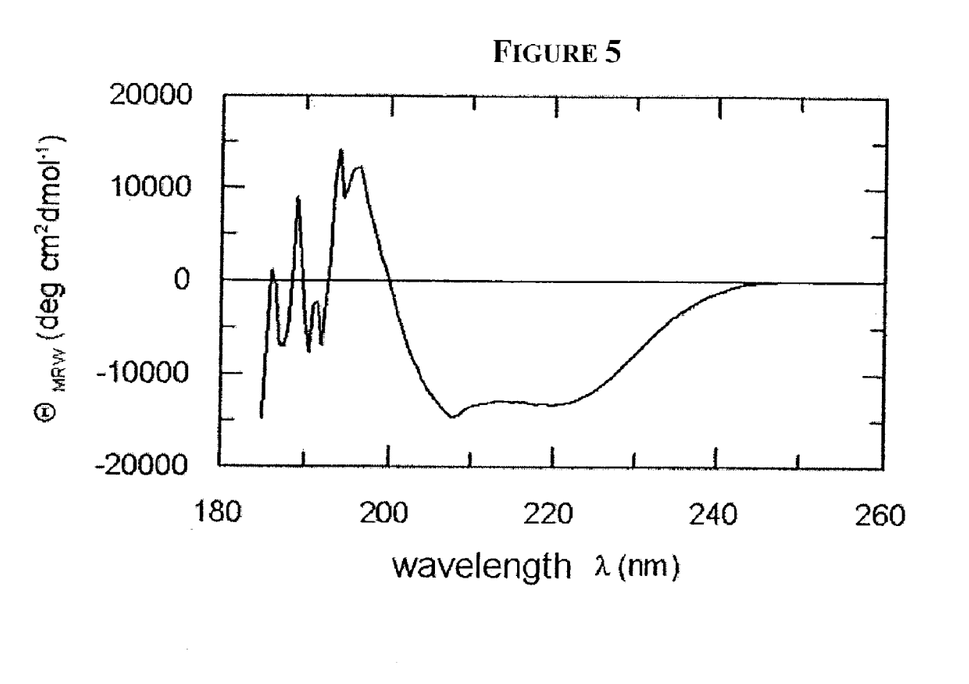
FIG. 5 Far UV CD of FkpA-gp41 under physiological buffer conditions.

The far UV CD of FkpA-gp41 at pH 7.4 (FIG. 5) confirms the near UV CD results in that it shows the additivity of the signal contributions of FkpA and gp41, respectively. As expected, the spectrum is dominated by the highly helical gp41 ectodomain (maximal ellipticity at 220 nm and 208 nm, respectively).

The data obtained with the covalently linked gp41/FkpA protein domains solubilized at pH 7.4 under the conditions mentioned above indicate that FkpA and gp41 behave as independently folding units within the polypeptide construct.

Example 2

Use of a SlyD-Based Expression Vector

The chaperone SlyD has been isolated by routine cloning procedures from *E. coli*. For recombinant expression, a DNA construct has been prepared coding for amino acids 1 to 165 of SlyD. An expression vector has been constructed comprising SlyD(1-165) as fusion partner and HIV-1 gp41 as target protein (cf.: SEQ ID NO:6). The fusion protein was expressed and successfully purified as described for FkpA-gp41 above. Interestingly, we found that a native-like fusion polypeptide of the SlyD(1-165)-gp41 type can be obtained in a very convenient manner by dialysis of the chaotropic material (dissolved, e.g. in 7.0 M GuHCl) against 50 mM sodium phosphate pH 7.4, 150 mM NaCl at room temperature.

Example 3

Purification of scFkpA and scSlyD

The single-chain PPIases scSlyD (SEQ ID NO:7) and scFkpA (SEQ ID NO: 8), respectively, were obtained from an *E. coli* overproducer according to virtually the same purification protocol as described in Example 1. In short: the induced cells were harvested, washed in PBS and lysed in 50 mM sodium phosphate pH 7.8, 100 mM sodium chloride, 7.0 M GuHCl at room temperature. The unfolded target proteins were bound to a Ni—NTA-column via their C-teminal hexa-His-tag and were refolded in 50 mM sodium phosphate, pH 7.8, 100 mM sodium chloride. After this matrix-assisted refolding procedure, the proteins were eluted in an imidazole gradient and subjected to a gel filtration on a Superdex 200® column.

Figure 6:
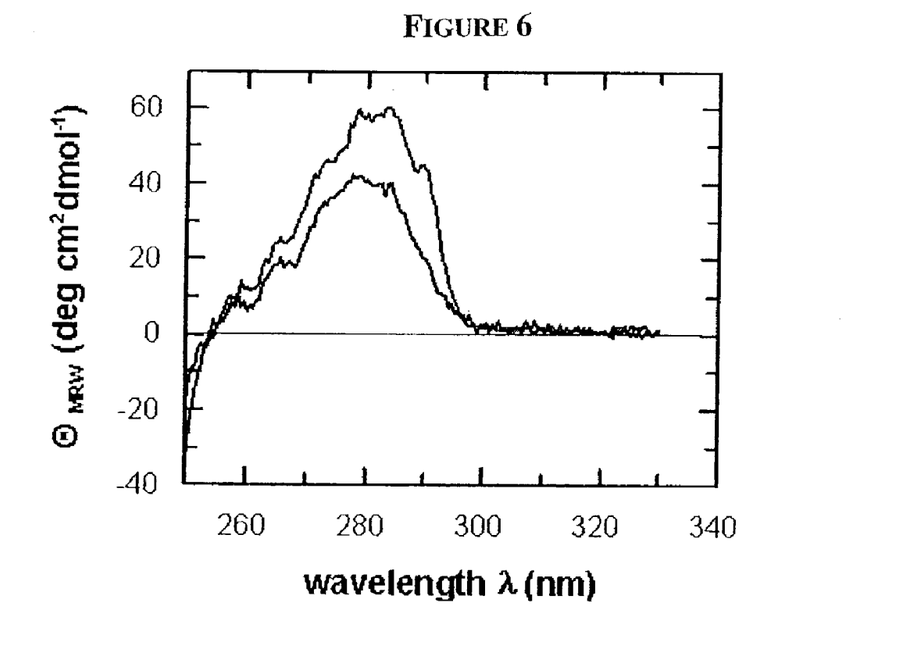
FIG. 6 The Near-UV-CD-spectra of scFkpA and scSlyD resemble each other

Alternatively, scSlyD and scFkpA may be dialysed after elution to remove residual concentrations of imidazole. Both proteins turn out to be highly soluble. ScSlyD, for example, does not tend to aggregate at concentrations up to 25 mg/ml. In order to elucidate the tertiary structure of the refolded scPPIases, we monitored CD-spectra in the Near-UV-region. The signatures of both scSlyD and scFkpA resemble each other and reflect the close relationship and thus structural homology of the two FKBPs. Due to the low content in aromatic residues, the signal intensity of scSlyD (FIG. 6) is, however, significantly lower than the one of scFkpA.

Example 4

Improved Expression of Target Proteins

The biochemically quite different target proteins HIV-1 gp41, HIV-2 gp36, HIV-1 p17 and HTLV gp21 have been expressed using the pET/BL21 expression system either without fusion partner (gp41, gp36, p17, gp21), or using same standard expression system, but comprising a DNA-construct coding for a fusion protein according to the present invention (SlyD-gp41, FkpA-gp41, FkpA-p17, SlyD-gp36, FkpA-gp21). The efficiency of these systems has been compared in terms of yield of recombinant protein per *E. coli* cell mass [mg/g]. As becomes readily obvious from Table 1, the novel expression systems lead to a significant improvement for all proteins tested.

TABLE 1

| Protein | Yield [mg protein/g *E. coli* cell mass] |
|---------|------------------------------------------|
| gp41 | ~1–2 |
| SlyD-gp41 | ~30 |
| FkpA-gp41 | ~25 |
| p17 | ~1 |
| FkpA-p17 | ~15 |
| gp36 | ~1–2 |
| SlyD-gp36 | ~45 |
| gp21 | ~4 |
| FkpA-gp21 | ~30 |

REFERENCES

Sambrook, J., et al., in "Molecular Cloning: A Laboratory Manual" (1989)-, Eds. J. Sambrook, E. F. Fritsch and T. Maniatis, Cold Spring Harbour Laboratory Press, Cold Spring Harbour, N.Y.

Beaucage, S. L. and Caruthers, M. H., Tetrahedron Letters 22 (1981) 1859-1862

Ausubel, F., et al., in "Current protocols in molecular biology" (1987 and periodic updates), Eds. F. Ausubel, R. Brent and K. R. E., Wiley & Sons Verlag, New York Fischer, G., et al., Nature 337 (1989) 476-8

Hottenrott, S., et a., J Biol Chem 272 (1997) 15697-701

Kapust, R. B. and Waugh, D. S., Protein Sci 8 (1999) 1668-74

Kay, J. E., Biochem J 314 (1996) 361-85

Lane, W. S., et al., J Protein Chem 10 (1991) 151-60

Matteucci, M. D. and Caruthers, M. H., J. Am. Chem. Soc. 103 (1981) 3185-3191

Metzger, D., et al., Nature 334 (1988) 31-6

Rahfeld, J. U., et al, FEBS Lett 352 (1994) 180-4
Ramm, K. and Pluckthun, A., J Biol Chem 275 (2000) 17106-13
Schmid, F. X., Molecular chaperones in the life cyle of proteins (1998) 361-389, Eds. A. L. Fink and Y. Goto, Marcel Decker In., New York
Scholz, C., et al., Embo J 16 (1997) 54-8
EP 293 249
WO 00/28011
WO 93/25533
WO 97/10253
WO 98/1349

The invention claimed is:

1. An isolated inclusion body, comprising a fusion polypeptide encoded by a recombinant DNA molecule comprising:
   a first nucleotide sequence coding for a target polypeptide; and
   a second nucleotide sequence coding for an FKBP chaperone located upstream to the first nucleotide sequence, wherein the FKBP chaperone is FkpA or SlyD, wherein the FkpA chaperone comprises amino acids 26-270 of a wild-type FkpA chaperone, wherein the SlyD chaperone comprises a C-terminally truncated wild-type SlyD chaperone that provides for a functional chaperone activity, and wherein the FKBP chaperone allows for a cytosolic expression and refolding of the fusion polypeptide.

2. The isolated inclusion body of claim 1, wherein the target polypeptide comprises a polypeptide comprising at least one diagnostically relevant epitope of an infectious organism.

3. An isolated inclusion body, comprising a fusion polypeptide encoded by a DNA molecule comprising:

a first nucleotide sequence coding for a target polypeptide;

a second nucleotide sequence coding for an FKBP chaperone located upstream to the first nucleotide sequence, wherein the FKBP chaperone is FkpA or SlyD, wherein the FkpA chaperone comprises amino acids 26-270 of a wild-type FkpA chaperone, wherein the SlyD chaperone comprises a C-terminally truncated wild-type SlyD chaperone that provides for a functional chaperone activity, and wherein the FKBP chaperone allows for a cytosolic expression and refolding of the fusion polypeptide; and a third nucleotide sequence coding for a first peptidic linker of 10-100 amino acids located between the first nucleotide sequence coding for the target polypeptide and the second nucleotide sequence coding for the FKBP chaperone.

4. The isolated inclusion body of claim 3, wherein the target polypeptide comprises a polypeptide comprising at least one diagnostically relevant epitope of an infectious organism.

5. The isolated inclusion body of claim 1 or 3, wherein the FKBP chaperone is a single FKBP chaperone polypeptide.

6. The isolated inclusion body of claim 1 or 3, wherein FKBP chaperone comprises a first and a second FKBP chaperone polypeptide sequence.

7. The isolated inclusion body of claim 1 or 3, wherein the second nucleotide sequence increases expression of the first nucleotide sequence as compared to expression of the first nucleotide sequence in the absence of the second nucleotide sequence.

8. The isolated inclusion body of claim 1 or 3, wherein the C-terminally truncated wild-type SlyD chaperone comprises amino acids 1-165 of the wild-type SlyD.

9. The isolated inclusion body of claim 1 or 3, wherein the C-terminally truncated wild-type SlyD chaperone comprises amino acids 1-165 of a wild-type *E. coli* SlyD.

10. The isolated inclusion body of claim 1 or 3, wherein the target polypeptide is selected from the group consisting of HIV-1 gp41, HIV-2 gp36, HTLV gp21, and HIV-1 p17.

11. The isolated inclusion body of claim 1 or 3, wherein the target polypeptide comprises a polypeptide from an infectious organism.

12. The isolated inclusion body of claim 1 or 3, wherein the FkpA chaperone comprises amino acids 26-270 of a wild-type *E. coli* FkpA.

13. The isolated inclusion body of claim 3, wherein the third nucleotide sequence encodes the first peptidic linker and encodes a second peptidic linker of 10-100 amino acids.

14. The isolated inclusion body of claim 13 wherein the first peptidic linker is different from the second peptidic linker.

15. The isolated inclusion body of claim 13 or 14, wherein at least one of the first peptidic linker or the second peptidic linker comprises a proteolytic cleavage site.

16. An isolated inclusion body, comprising a recombinantly-produced fusion polypeptide comprising:

a target polypeptide;

a first and a second FKBP chaperone sequences selected from the group consisting of FkpA and SlyD, wherein the FkpA chaperone comprises amino acids 26-270 of a wild-type FkpA chaperone, wherein the SlyD chaperone comprises a C-terminally truncated wild-type SlyD chaperone that provides for a functional chaperone activity, wherein the first and the second FKBP chaperone sequences allow for a cytosolic expression and refolding of the fusion polypeptide; and a first and a second peptidic linker of 10-100 amino acids.

17. The isolated inclusion body of claim 16, wherein the target polypeptide comprises a polypeptide from an infectious organism.

18. The isolated inclusion body of claim 17, wherein the target polypeptide comprises at least one diagnostically relevant epitope of the infectious organism.

19. The isolated inclusion body of claim 16, wherein the first and the second FKBP chaperone sequences are located N-terminal with respect to the target polypeptide.

20. The isolated inclusion body of claim 16, wherein the first FKBP chaperone sequence is located N-terminal and the second FKBP chaperone sequence is located C-terminal with respect to the target polypeptide.

* * * * *